US010973647B2

(12) United States Patent
Tsai et al.

(10) Patent No.: US 10,973,647 B2
(45) Date of Patent: Apr. 13, 2021

(54) ARTIFICIAL JOINT

(71) Applicants: Industrial Technology Research Institute, Hsinchu (TW); National Taiwan University Hospital, Taipei (TW)

(72) Inventors: Pei-I Tsai, Hsinchu (TW); Hsin-Hsin Shen, Hsinchu County (TW); Kuo-Yi Yang, Hsinchu (TW); De-Yau Lin, Tainan (TW); Yi-Hung Wen, Hsinchu (TW); Chih-Chieh Huang, Miaoli County (TW); Wei-Luan Fan, Miaoli County (TW); Pei-Yu Chen, New Taipei (TW); Ching-Chi Hsu, New Taipei (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 120 days.

(21) Appl. No.: 16/224,809

(22) Filed: Dec. 19, 2018

(65) Prior Publication Data

US 2019/0388230 A1    Dec. 26, 2019

(30) Foreign Application Priority Data

Jun. 22, 2018   (TW) .................................. 107121576

(51) Int. Cl.
*A61F 2/42*    (2006.01)

(52) U.S. Cl.
CPC .... *A61F 2/4202* (2013.01); *A61F 2002/4205* (2013.01); *A61F 2002/4207* (2013.01); *A61F 2220/0033* (2013.01)

(58) Field of Classification Search
CPC ................ A61F 2/42–4297; A61F 2/38; A61F 2002/3863; A61F 2/385; A61F 2/3804; A61F 2/44; A61F 2/4425; A61F 2002/443
See application file for complete search history.

(56) References Cited

U.S. PATENT DOCUMENTS 4,156,944 A * 6/1979 Schreiber .............. A61F 2/4202
                                                    623/21.18
5,236,461 A * 8/1993 Forte ..................... A61F 2/3845
                                                    623/20.27
(Continued)

FOREIGN PATENT DOCUMENTS

AU       2003235085      3/2004
CN        203724275      7/2014
(Continued)

OTHER PUBLICATIONS

Joshua N. Tennant, et al., "Risks to the Blood Supply of the Talus with Four Methods of Total Ankle Arthroplasty," The Journal of Bone and Joint Surgery, vol. 96, Mar. 2014, pp. 395-402.
(Continued)

*Primary Examiner* — Alvin J Stewart
(74) *Attorney, Agent, or Firm* — JCIPRNET

(57) ABSTRACT

An artificial joint includes a first joint assembly and a second joint assembly. The first joint assembly is adapted to be connected to a first bone and has a first contacting surface, wherein the first contacting surface includes a first convex arc surface, a second convex arc surface, and a third convex arc surface. The second joint assembly is adapted to be connected to a second bone and has a second contacting surface, wherein the second contacting surface is in contact with the first contacting surface and includes a first concave arc surface, a second concave arc surface, and a third concave arc surface, and the first concave arc surface, the second concave arc surface, and the third concave arc
(Continued)

surface respectively correspond to the first convex arc surface, the second convex arc surface, and the third convex arc surface.

15 Claims, 12 Drawing Sheets

(56) References Cited

U.S. PATENT DOCUMENTS

| | | | | |
|---|---|---|---|---|
| 5,358,527 | A * | 10/1994 | Forte | A61F 2/3845 |
| | | | | 623/20.27 |
| 5,425,773 | A * | 6/1995 | Boyd | A61F 2/4425 |
| | | | | 623/17.15 |
| 5,766,259 | A * | 6/1998 | Sammarco | A61F 2/4606 |
| | | | | 623/21.18 |
| 6,039,763 | A * | 3/2000 | Shelokov | A61F 2/4425 |
| | | | | 623/17.16 |
| 6,183,519 | B1 * | 2/2001 | Bonnin | A61F 2/4202 |
| | | | | 623/21.11 |
| 6,203,576 | B1 * | 3/2001 | Afriat | A61F 2/3868 |
| | | | | 623/20.18 |
| 6,699,291 | B1 * | 3/2004 | Augoyard | A61F 2/3886 |
| | | | | 623/20.24 |
| 7,485,147 | B2 | 2/2009 | Pappas et al. | |
| 7,534,270 | B2 * | 5/2009 | Ball | A61F 2/4202 |
| | | | | 623/21.18 |
| 7,550,009 | B2 * | 6/2009 | Arnin | A61F 2/4425 |
| | | | | 623/17.15 |
| 7,615,082 | B2 * | 11/2009 | Naegerl | A61F 2/4202 |
| | | | | 623/21.18 |
| 7,625,409 | B2 * | 12/2009 | Saltzman | A61B 17/15 |
| | | | | 623/21.18 |
| 7,815,684 | B2 * | 10/2010 | McMinn | A61F 2/3859 |
| | | | | 623/20.27 |
| 7,955,394 | B2 * | 6/2011 | Hotokebuchi | A61F 2/3886 |
| | | | | 623/20.14 |
| 7,963,996 | B2 * | 6/2011 | Saltzman | A61B 17/15 |
| | | | | 623/21.18 |
| 8,163,023 | B2 * | 4/2012 | Nguyen | A61F 2/4425 |
| | | | | 623/17.14 |
| 8,292,964 | B2 * | 10/2012 | Walker | A61F 2/3859 |
| | | | | 623/20.21 |
| 8,540,776 | B2 * | 9/2013 | Bercovy | A61F 2/3868 |
| | | | | 623/20.21 |
| 8,632,600 | B2 | 1/2014 | Zannis et al. | |
| 8,668,743 | B2 * | 3/2014 | Perler | A61F 2/4202 |
| | | | | 623/21.18 |
| 8,728,163 | B2 * | 5/2014 | Theofilos | A61F 2/4425 |
| | | | | 623/17.15 |
| 8,858,644 | B2 * | 10/2014 | Goubau | A61F 2/4241 |
| | | | | 623/21.15 |
| 9,132,019 | B2 * | 9/2015 | Weems | A61F 2/4225 |
| 9,248,024 | B2 * | 2/2016 | Ferrari | A61F 2/4202 |
| 9,468,532 | B2 * | 10/2016 | Perler | A61F 2/4202 |
| 9,610,168 | B2 * | 4/2017 | Terrill | A61F 2/4202 |
| 9,833,323 | B2 * | 12/2017 | Richter | A61F 2/3886 |
| 10,667,920 | B2 * | 6/2020 | Sedel | A61F 2/3859 |
| 2004/0039394 | A1 | 2/2004 | Conti et al. | |
| 2006/0142870 | A1 * | 6/2006 | Robinson | A61B 17/142 |
| | | | | 623/21.18 |
| 2006/0247788 | A1 | 11/2006 | Ross | |
| 2007/0112431 | A1 * | 5/2007 | Kofoed | A61F 2/30734 |
| | | | | 623/21.18 |
| 2009/0036992 | A1 | 2/2009 | Tsakonas | |
| 2009/0234360 | A1 | 9/2009 | Alexander | |
| 2012/0271430 | A1 | 10/2012 | Arnett et al. | |
| 2014/0046452 | A1 | 2/2014 | Walker | |
| 2014/0107799 | A1 | 4/2014 | Tuke et al. | |
| 2014/0135939 | A1 * | 5/2014 | Petteys | A61F 2/4202 |
| | | | | 623/21.18 |
| 2014/0236157 | A1 * | 8/2014 | Tochigi | A61B 17/15 |
| | | | | 606/87 |
| 2014/0296995 | A1 | 10/2014 | Reiley et al. | |
| 2015/0045902 | A1 * | 2/2015 | Perler | A61F 2/4202 |
| | | | | 623/21.18 |
| 2015/0057761 | A1 * | 2/2015 | Smirthwaite | A61F 2/4202 |
| | | | | 623/21.18 |
| 2016/0206437 | A1 * | 7/2016 | Perler | A61F 2/4202 |
| 2019/0059917 | A1 * | 2/2019 | Saltzman | A61B 17/1682 |
| 2019/0070012 | A1 * | 3/2019 | Leemrijse | A61F 2/4202 |
| 2019/0350717 | A1 * | 11/2019 | Tuttle | A61B 17/866 |
| 2020/0197187 | A1 * | 6/2020 | Lee | A61F 2/4202 |
| 2020/0268520 | A1 * | 8/2020 | Pak | A61F 2/389 |

FOREIGN PATENT DOCUMENTS

| | | |
|---|---|---|
| CN | 103417313 | 7/2016 |
| CN | 106473842 | 3/2017 |
| TW | M521999 | 5/2016 |
| WO | 2015175560 | 11/2015 |

OTHER PUBLICATIONS

John S. Lewis Jr, et al., "Comparison of First- and Second-Generation Fixed-Bearing Total Ankle Arthroplasty Using a Modular Intramedullary Tibial Component," Foot & Ankle International, Mar. 2015, pp. 1-10.

Gregory A Lundeen, et al., "Motion at the Tibial and Polyethylene Component Interface in a Mobile-Bearing Total Ankle Replacement," Foot & Ankle International, Apr. 2016, pp. 1-7.

Jessica E. Goetz, et al., "Variable Volumes of Resected Bone Resulting From Different Total Ankle Arthroplasty Systems," Foot & Ankle International, Apr. 2016, pp. 1-7.

N. Espinosa, et al., "Misalignment of Total Ankle Components Can Induce High Joint Contact Pressures," The Journal of Bone and Joint Surgery, May 2010, pp. 1179-1187.

Christopher Bibbo, "Controversies in Total Ankle Replacement," Clin Podiatr Med Surg, Oct. 2012, pp. 21-34.

Andrea Cracchiolo III, MD, et al., "Design Features of Current Total Ankle Replacements: Implants and Instrumentation," Journal of the American Academy of Orthopaedic Surgeons, Sep. 2008, pp. 530-540.

Bradley Jay Elliot, et al., "Finite element analysis of stress and wear characterization in total ankle replacements," Journal of the Mechanical Behavior of Biomedical Materials, Jan. 2014, pp. 134-145.

Alberto Leardini, et al., "Biomechanics of the natural, arthritic, and replaced human ankle joint," Journal of Foot and Ankle Research, Feb. 2014, pp. 1-16.

Michael J. Pappas, PHD, et al., "Failure Modes of Current Total Ankle Replacement Systems," Clinics in Podiatric Medicine and Surgery, Apr. 2013, pp. 123-143.

John J. Yu, M.D., et al., "Total Ankle Replacement Evolution of the Technology and Future Applications," Bulletin of the Hospital for Joint Diseases, Aug. 2014, pp. 120-128.

B. Reggiani, et al., "Finite element analysis of a total ankle replacement during the stance phase of gait," Journal of Biomechanics, vol. 39, Apr. 2005, pp. 1435-1443.

Mustafa Ozen, et al., "Modeling and stress analyses of a normal foot-ankle and a prosthetic foot-ankle complex," Acta of Bioengineering and Biomechanics, vol. 15, Mar. 2013, pp. 19-27.

"Office Action of Taiwan Counterpart Application," dated Jan. 20, 2020, p. 1-p. 8.

"Search Report of Europe Counterpart Application", dated Jul. 4, 2019, pp. 1-8.

* cited by examiner

10,973,647 B2

ARTIFICIAL JOINT

CROSS-REFERENCE TO RELATED APPLICATION

This application claims the priority benefit of Taiwan application serial no. 107121576, filed on Jun. 22, 2018. The entirety of the above-mentioned patent application is hereby incorporated by reference herein and made a part of this specification.

BACKGROUND

Technical Field

The disclosure relates to a human body implant, and in particular, to an artificial joint.

Description of Related Art

If an artificial joint is not in sufficient coordination with bone and ligament structures of the human body, additional stress and wearing or loosening of the artificial joint may occur during motions of the joint. Compared to the knee joint and the hip joint, motions of the ankle joint are subjected to greater restraint by the bone and ligament structures. Therefore, the error tolerance for mounting an artificial ankle joint in a surgery is fairly limited, and additional stress, wearing, and loosening mentioned above are more likely to occur. For this reason, the ten-year survival rate of the current artificial ankle joints is about 80%, which is still lower than that of the artificial knee joints (95%). Accordingly, in an artificial ankle joint system, in addition to developing surgical appliances with higher precision to reduce the mounting error in the surgery, motion allowance should also be increased in the design of the artificial ankle joint to provide fault tolerance.

SUMMARY

The artificial joint of the disclosure includes a first joint assembly and a second joint assembly. The first joint assembly is adapted to be connected to a first bone and has a first contacting surface, wherein the first contacting surface includes a first convex arc surface, a second convex arc surface, and a third convex arc surface. The second joint assembly is adapted to be connected to a second bone and has a second contacting surface, wherein the second contacting surface is in contact with the first contacting surface and includes a first concave arc surface, a second concave arc surface, and a third concave arc surface, and the first concave arc surface, the second concave arc surface, and the third concave arc surface respectively correspond to the first convex arc surface, the second convex arc surface, and the third convex arc surface.

To provide a further understanding of the aforementioned and other content of the disclosure, exemplary embodiments, together with the reference drawings, are described in detail below.

BRIEF DESCRIPTION OF THE DRAWINGS

The accompanying drawings are included to provide a further understanding of the disclosure and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
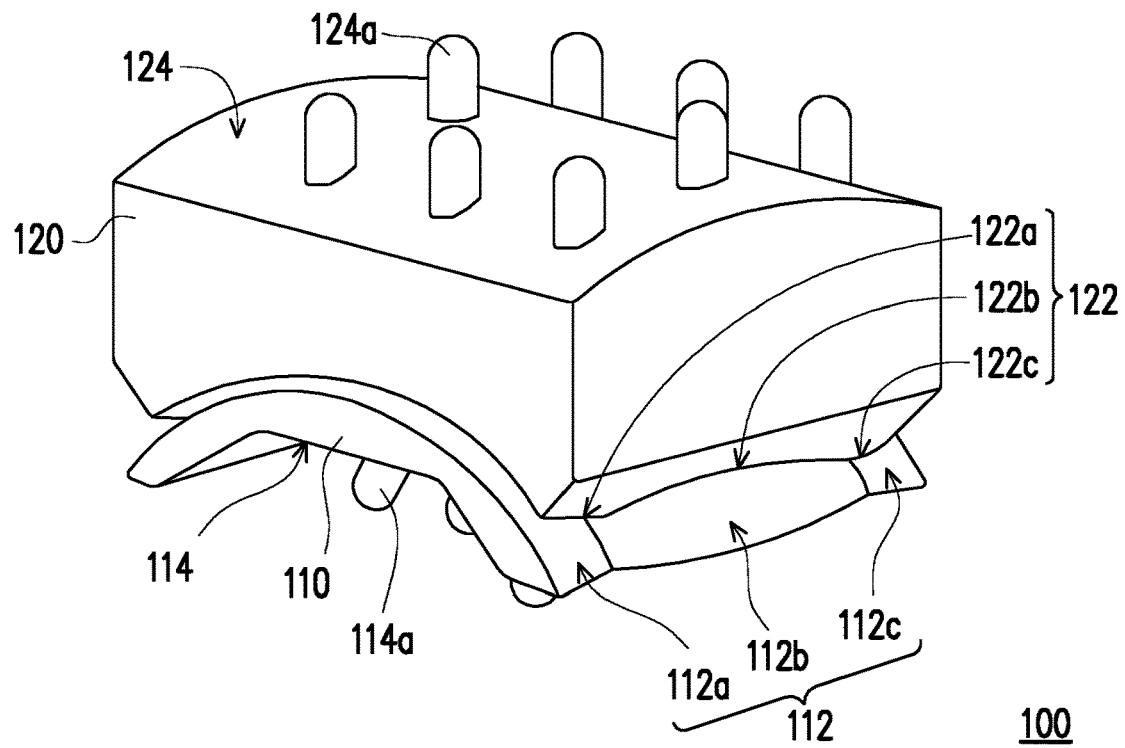
FIG. 1 is a perspective view illustrating an artificial joint of an embodiment of the disclosure.

Some other embodiments of the disclosure are provided as follows. It should be noted that the reference numerals and part of the contents of the previous embodiment are used in the following embodiments, in which identical reference numerals indicate identical or similar components, and repeated description of the same technical contents is omitted. Please refer to the description of the previous embodiment for the omitted contents, which will not be repeated hereinafter.

The disclosure provides an artificial joint in which stress, wearing, and loosening can be mitigated.

Figure 2:
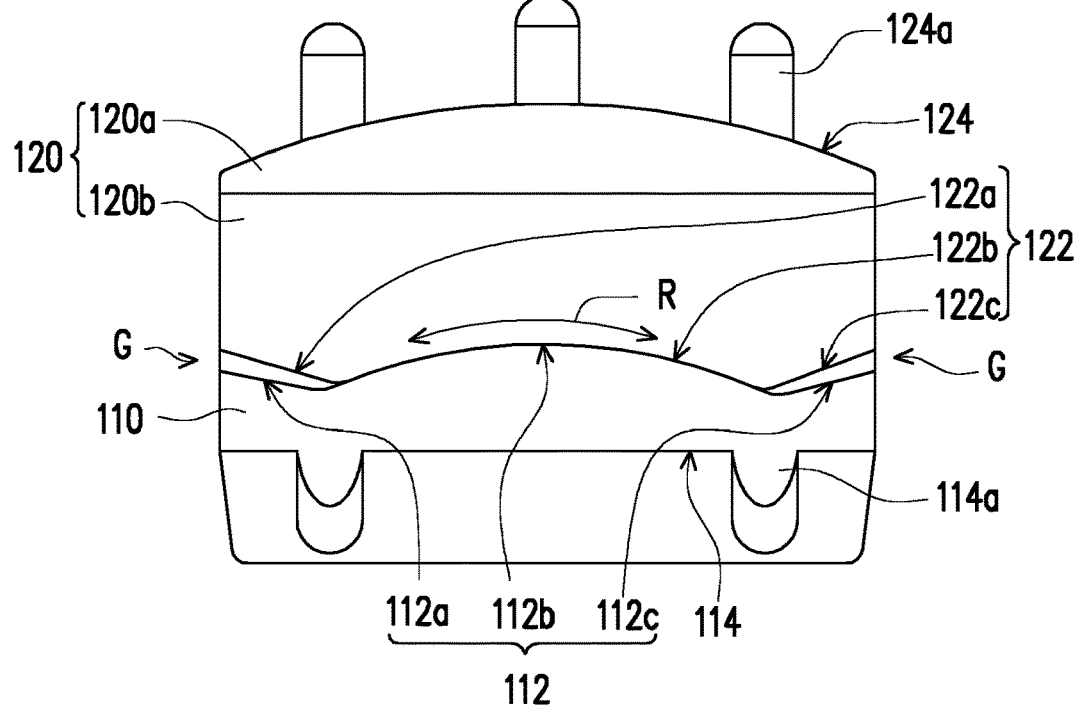
FIG. 2 is a cross-sectional view illustrating the artificial joint of FIG. 1.

FIG. 1 is a perspective view illustrating an artificial joint of an embodiment of the disclosure. FIG. 2 is a cross-sectional view illustrating the artificial joint of FIG. 1. Referring to FIG. 1 and FIG. 2, an artificial joint 100 of the present embodiment is, for example, an artificial ankle joint and includes a first joint assembly 110 and a second joint assembly 120. The first joint assembly 110 is adapted to be connected to a first bone such as a talus, and the first joint assembly 110 has a first contacting surface 112. The second joint assembly 120 is adapted to be connected to a second bone such as a tibia, and the second joint assembly 120 has a second contacting surface 122, wherein the second contacting surface 122 is in contact with the first contacting surface 112. The artificial joint 100 simulates motion of the human body joint through relative sliding of the first contacting surface 112 and the second contacting surface 122.

Specifically, the first contacting surface 112 includes a first convex arc surface 112a, a second convex arc surface 112b, and a third convex arc surface 112c, and the second convex arc surface 112b is connected between the first convex arc surface 112a and the third convex arc surface 112c. The second contacting surface 122 includes a first concave arc surface 122a, a second concave arc surface 122b, and a third concave arc surface 122c, and the second concave arc surface 122b is connected between the first concave arc surface 122a and the third concave arc surface 122c. The first concave arc surface 122a, the second concave arc surface 122b, and the third concave arc surface 122c respectively correspond to the first convex arc surface 112a, the second convex arc surface 112b, and the third convex arc surface 112c.

In such a design, the second convex arc surface 112b and the second concave arc surface 122b located in the middle can be in contact with each other to provide support. When the second convex arc surface 112b and the second concave arc surface 122b are in normal contact with each other, a gap G is present between the first convex arc surface 112a and the first concave arc surface 122a located on one outer side, and another gap G is present between the third convex arc surface 112c and the third concave arc surface 122c located on the other outer side, which increases a space for relative motion of the first joint assembly 112 and the second joint assembly 122, such that the second convex arc surface 112b and the second concave arc surface 122b can slide relatively in a direct R (labeled in FIG. 2); namely, after implantation is performed, there are an inversion angle allowance and an eversion angle allowance. Moreover, the second convex arc surface 112b and the second concave arc surface 122b can rotate relatively along an axis Z (labeled in FIG. 2); namely, after implantation is performed, there are an internal rotation angle allowance and an external rotation angle allowance. Accordingly, additional stress between the first joint assembly 112 and the second joint assembly 122 due to structural restriction of bones and ligaments can be reduced, and wearing and loosening of the artificial joint 100 can be mitigated.

In other embodiments, it is possible that no gap or a smaller gap is present between the first convex arc surface 112a and the first concave arc surface 122a and between the third convex arc surface 112c and the third concave arc surface 122c, which may be tested and selected by the surgeon in a joint replacement surgery.

Furthermore, in the present embodiment, an area of the second convex arc surface 112b is greater than an area of the first convex arc surface 112a and greater than an area of the third convex arc surface 112c, and an area of the second concave arc surface 122b is greater than an area of the first concave arc surface 122a and greater than an area of the third concave arc surface 122c. Designing the second convex arc surface 112b and the second concave arc surface 122b located in the middle to have a greater area as described above allows them to provide the main weight-bearing function. The first convex arc surface 112a, the first concave arc surface 122a, the third convex arc surface 112c, and the third concave arc surface 122c located on the outer sides having a smaller area may provide inversion and eversion stability after implantation is performed.

In the present embodiment, the first convex arc surface 112a, the second convex arc surface 112b, and the third convex arc surface 112c are all, for example, convex spherical surfaces, and the first concave arc surface 122a, the second concave arc surface 122b, and the third concave arc surface 122c are all, for example, concave spherical surfaces. However, the disclosure is not limited thereto. In other embodiments, it is possible that the second convex arc surface 112b and the second concave arc surface 122b are spherical surfaces, and the first convex arc surface 112a, the third convex arc surface 112c, the first concave arc surface 122a, and the third concave arc surface 122c are aspherical surfaces.

Figure 3:
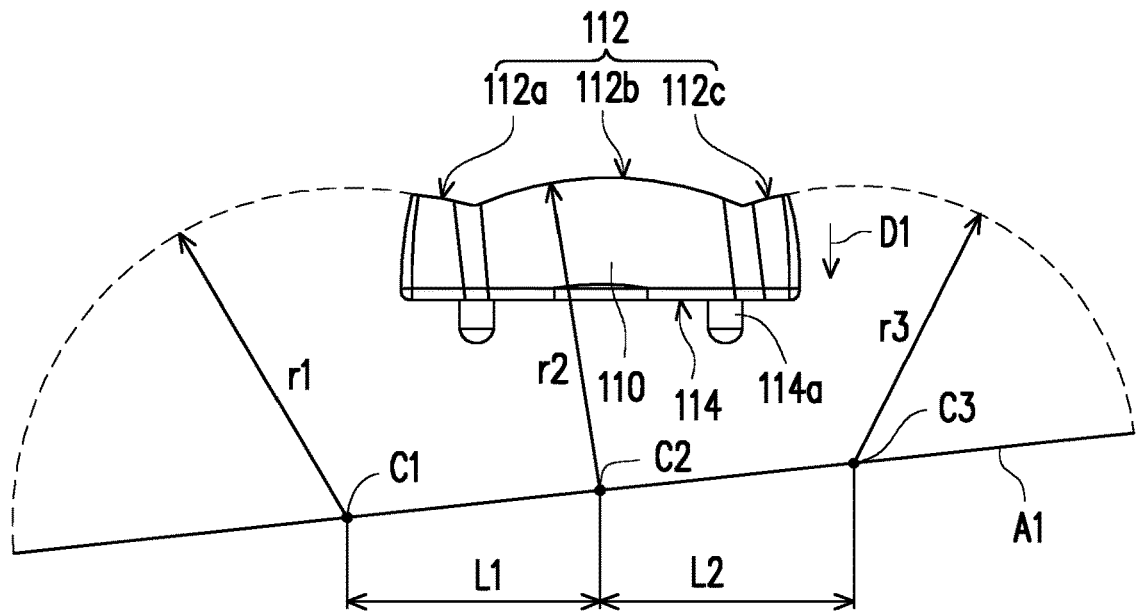
FIG. 3 is a front view illustrating a first joint assembly of FIG. 1.
Figure 4:
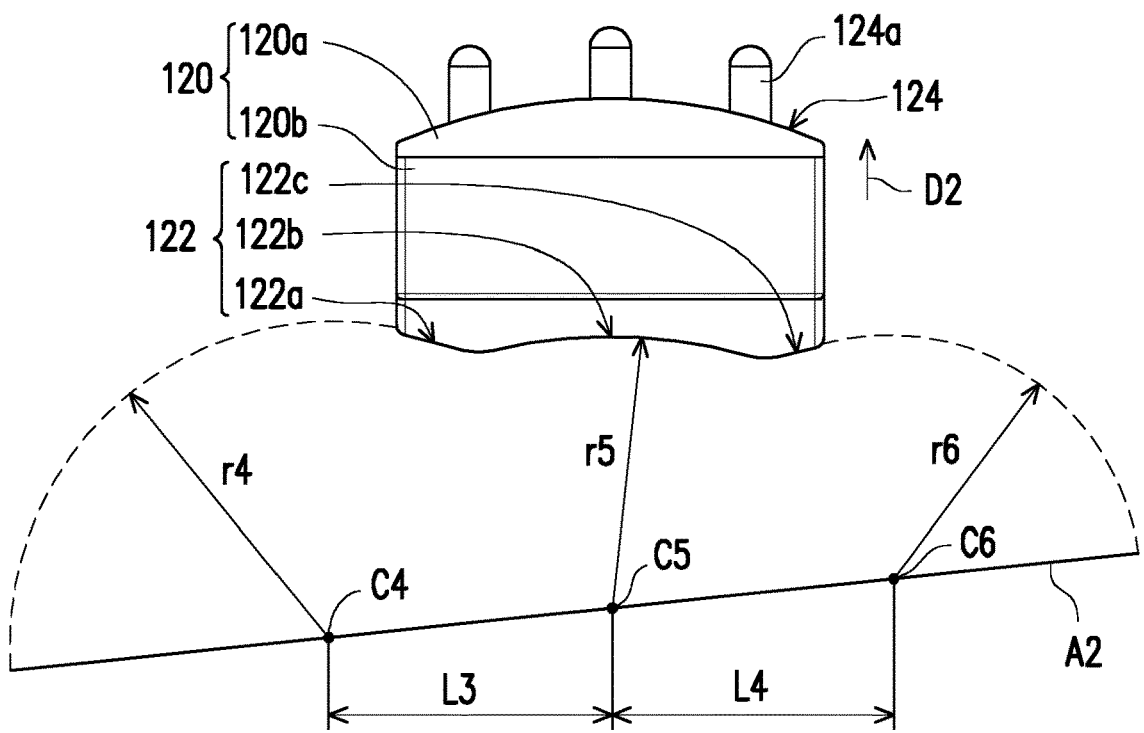
FIG. 4 is a front view illustrating a part of the structure of a second joint assembly of FIG. 1.

Designs of the arc surfaces will be detailed below. FIG. 3 is a front view illustrating the first joint assembly of FIG. 1. FIG. 4 is a front view illustrating a part of the structure of the second joint assembly of FIG. 1. Referring to FIG. 3 and FIG. 4, in the present embodiment, centers C1, C2, C3 of curvature of the first convex arc surface 112a, the second convex arc surface 112b, and the third convex arc surface 112c are different, and centers C4, C5, C6 of curvature of the first concave arc surface 122a, the second concave arc surface 122b, and the third concave arc surface 122c are different. The first joint assembly 110 is adapted to be connected to the first bone in a direction D1. A connecting line A1 of the center C1 of curvature of the first convex arc surface 112a, the center C2 of curvature of the second convex arc surface 112b, and the center C3 of curvature of the third convex arc surface 112c is not perpendicular to the direction D1, and an inclination angle is present between the connecting line A1 and the horizontal direction. The second joint assembly 120 is adapted to be connected to the second bone in a direction D2. A connecting line A2 of the center C4 of curvature of the first concave arc surface 122a, the center C5 of curvature of the second concave arc surface 122b, and the center C6 of curvature of the third concave arc surface 122c is not perpendicular to the direction D2, and an inclination angle is present between the connecting line A2 and the horizontal direction. In other embodiments, the connecting line A1 may also be perpendicular to the direction D1 and the connecting line A2 may also be perpendicular to the direction D2, and the disclosure is not limited thereto.

Moreover, although the centers C1, C2, C3 of curvature are shown to be located on the straight connecting line A1 and the centers C4, C5, C6 of curvature are shown to be located on the straight connecting line A2 in FIG. 3 and FIG. 4, the connecting line of the centers C1, C2 of curvature may be actually designed not to be parallel to the connecting line of the centers C2, C3 of curvature, and/or the connecting line of the centers C4, C5 of curvature may be designed not to be parallel to the connecting line of the centers C5, C6 of curvature. In addition, the inclination angle of the connecting line of the centers C1, C2 of curvature may be designed to be different from the inclination angle of the connecting line of the centers C4, C5 of curvature, and the inclination angle of the connecting line of the centers C2, C3 of curvature may be designed to be different from the inclination angle of the connecting line of the centers C5, C6 of curvature, such that the gap G can be present respectively between the first convex arc surface 112a and the first concave arc surface 122a and between the third convex arc surface 112c and the third concave arc surface 122c as shown in FIG. 2, and allowances for inversion, eversion, internal rotation, and external rotation can thereby be provided after implantation is performed. Moreover, in other embodiments where the first convex arc surface 112a, the third convex arc surface 112c, the first concave arc surface 122a, and the third concave arc surface 122c are not spherical surfaces, the gap G may similarly be present respectively between the first convex arc surface 112a and the first concave arc surface 122a and between the third convex arc surface 112c and the third concave arc surface 122c through a suitable geometric design to thereby provide allowances for inversion, eversion, internal rotation, and external rotation after implantation is performed.

More specifically, a radius r2 of curvature of the second convex arc surface 112b may be, for example, 15 to 35 mm, may be 20 to 30 mm in an embodiment, or may be designed to be 25 mm. The value varies depending on the corresponding bone size of the human body (generally 17 to 33 mm). The inclination angle of the connecting line A1 with respect to the horizontal direction may be, for example, 0 to 10 degrees, may be 4 to 8 degrees in an embodiment, or may be designed to be 6 degrees, which is in line with the average inclination angle for normal physiological motions of the ankle joint. The horizontal direction is perpendicular to the direction D1. A distance L1 between the center C1 of curvature of the first convex arc surface 112a and the center C2 of curvature of the second convex arc surface 112b in the horizontal direction may be, for example, 5 to 30 mm and may be 20 mm in an embodiment. A distance L2 between the center C3 of curvature of the third convex arc surface 112c and the center C2 of curvature of the second convex arc surface 112b in the horizontal direction may be, for example, 5 to 30 mm and may be 20 mm in an embodiment. A radius r1 of curvature of the first convex arc surface 112a may be, for example, 15 to 38.53 mm, may be 21.4 to 32.81 mm in an embodiment, or may be designed to be 27.1 mm. A radius r3 of curvature of the third convex arc surface 112c may be, for example, 11.47 to 35 mm, may be 17.19 to 28.6 mm in an embodiment, or may be designed to be 22.9 mm. The radii r1, r3 of curvature are obtained by calculation based on the radius r2 of curvature, the distance L1, the distance L2, a length of the connecting line of the centers C1 and C2 of curvature, and a length of the connecting line of the centers C2 and C3 of curvature.

It is noted that, in the case where the connecting line of the centers C1, C2 of curvature is designed not to be parallel to the connecting line of the centers C2, C3 of curvature as described above, the inclination angle of the connecting line of the centers C1, C2 of curvature may be, for example, 2 to 14 degrees, may be 6 to 10 degrees in an embodiment, or may be designed to be 8 degrees, and the inclination angle of the connecting line of the centers C2, C3 of curvature may be, for example, −2 to 10 degrees, may be 2 to 6 degrees in an embodiment, or may be designed to be 4 degrees. Therefore, the radius r1 of curvature and the radius r3 of curvature also change accordingly.

A radius r5 of curvature of the second concave arc surface 122b may be, for example, 15 to 35 mm, may be 20 to 30 mm in an embodiment, or may be designed to be 25 mm, which depends on the corresponding bone size of the human body (generally 17 to 33 mm). The inclination angle of the connecting line A2 with respect to the horizontal direction may be, for example, 0 to 10 degrees, may be 4 to 8 degrees in an embodiment, or may be designed to be 6 degrees, which is in line with the average inclination angle for normal physiological motions of the ankle joint. The horizontal direction is perpendicular to the direction D2. A distance L3 between the center C4 of curvature of the first concave arc surface 122a and the center C5 of curvature of the second concave arc surface 122b in the horizontal direction may be, for example, 5 to 30 mm and may be 20 mm in an embodiment. A distance L4 between the center C6 of curvature of the third concave arc surface 122c and the center C5 of curvature of the second concave arc surface 122b in the horizontal direction may be, for example, 5 to 30 mm and may be 20 mm in an embodiment. A radius r4 of curvature of the first concave arc surface 122a may be, for example, 15 to 38.53 mm, may be 21.4 to 32.81 mm in an embodiment, or may be designed to be 27.1 mm. A radius r6 of curvature of the third concave arc surface 122c may be, for example, 11.47 to 35 mm, may be 17.19 to 28.6 mm in an embodiment, or may be designed to be 22.9 mm. The radii r4, r6 of curvature are obtained by calculation based on the radius r5 of curvature, the distance L3, the distance L4, a length of the connecting line of the centers C4 and C5 of curvature, and a length of the connecting line of the centers C5 and C6 of curvature.

It is noted that, in the case where the connecting line of the centers C4, C5 of curvature is designed not to be parallel to the connecting line of the centers C5, C6 of curvature as described above, the inclination angle of the connecting line of the centers C4, C5 of curvature may be, for example, −2 to 10 degrees, may be 2 to 8 degrees in an embodiment, or may be designed to be 6 degrees, and the inclination angle of the connecting line of the centers C5, C6 of curvature may be, for example, 2 to 14 degrees, may be 4 to 10 degrees in an embodiment, or may be designed to be 6 degrees. Therefore, the radius r4 of curvature and the radius r6 of curvature also change accordingly.

Referring to FIG. 1 and FIG. 2, the first joint assembly 110 of the present embodiment has a first connecting surface 114 opposite to the first contacting surface 112. The first connecting surface 114 includes a plurality of bone pegs 114a and is adapted to be connected to the first bone through the bone pegs 114a. Similarly, the second joint assembly 120 has a second connecting surface 124 opposite to the second contacting surface 122. The second connecting surface 124 includes a plurality of bone pegs 124a and is adapted to be connected to the second bone through the bone pegs 124a. Since the numbers of the bone pegs 114a and the bone pegs 124a are both plural, they can distribute the pressure between the first bone and the first joint assembly 110 and the pressure between the second bone and the second joint assembly 120 and further prevent stress concentration.

Figure 5:
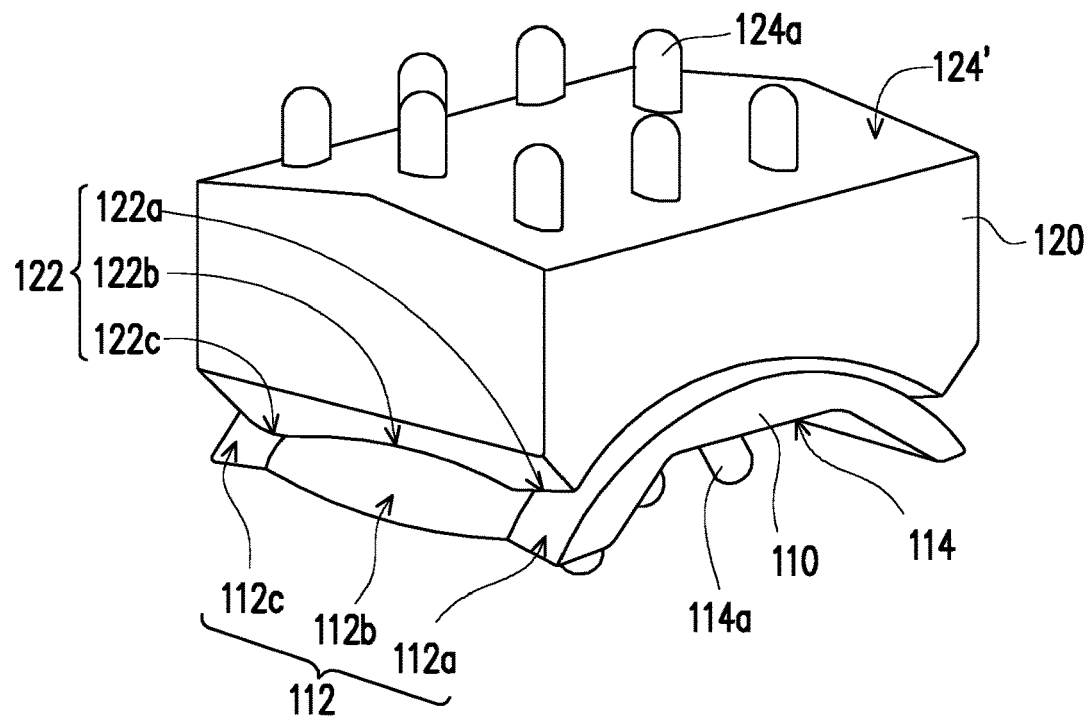
FIG. 5 is a perspective view illustrating an artificial joint of another embodiment of the disclosure.
Figure 6:
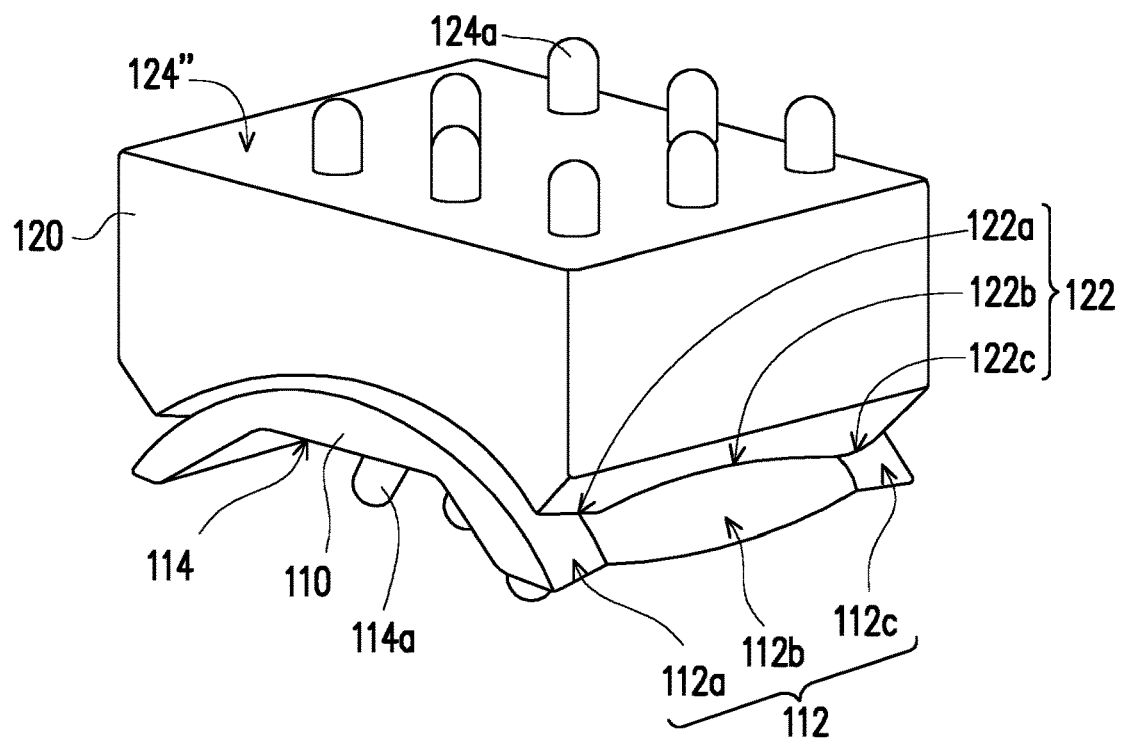
FIG. 6 is a perspective view illustrating an artificial joint of another embodiment of the disclosure.

In the present embodiment, the first connecting surface 114 of the first joint assembly 110 is a concave surface. Moreover, the second connecting surface 124 of the second joint assembly 120 is a convex arc surface to distribute the pressure between the second bone and the second joint assembly 120. However, the disclosure is not limited thereto and will be further illustrated below with reference to the drawings. FIG. 5 is a perspective view illustrating an artificial joint of another embodiment of the disclosure. The embodiment shown in FIG. 5 is similar to the embodiment shown in FIG. 1. It is noted that a second connecting surface 124' of the second joint assembly 120 of FIG. 5 is a pitched surface. FIG. 6 is a perspective view illustrating an artificial joint of another embodiment of the disclosure. The embodiment shown in FIG. 6 is similar to the embodiment shown in FIG. 1. It is noted that a second connecting surface 124" of the second joint assembly 120 of FIG. 6 is a plane.

In the embodiment shown in FIG. 1 and FIG. 2, the second joint assembly 120 is formed of a connecting member 120a and a contacting member 120b, and the connecting member 120a and the contacting member 120b are joined and fixed together. In the case where the artificial joint 100 is used as an artificial ankle joint, the first joint assembly 110 is a talar component used to be connected to a talus, the connecting member 120a is a tibial component used to be connected to a tibia, and the contacting member 120b is an insert located between the talar component and the tibial component. The material of the connecting member 120a and the first joint assembly 110 is, for example, metal, and the material of the contacting member 120b is, for example, plastic. In other embodiments, the connecting member 120a, the first joint assembly 110, and the contacting member 120b may be respectively formed of other suitable materials, and the disclosure is not limited thereto.

Figure 7:
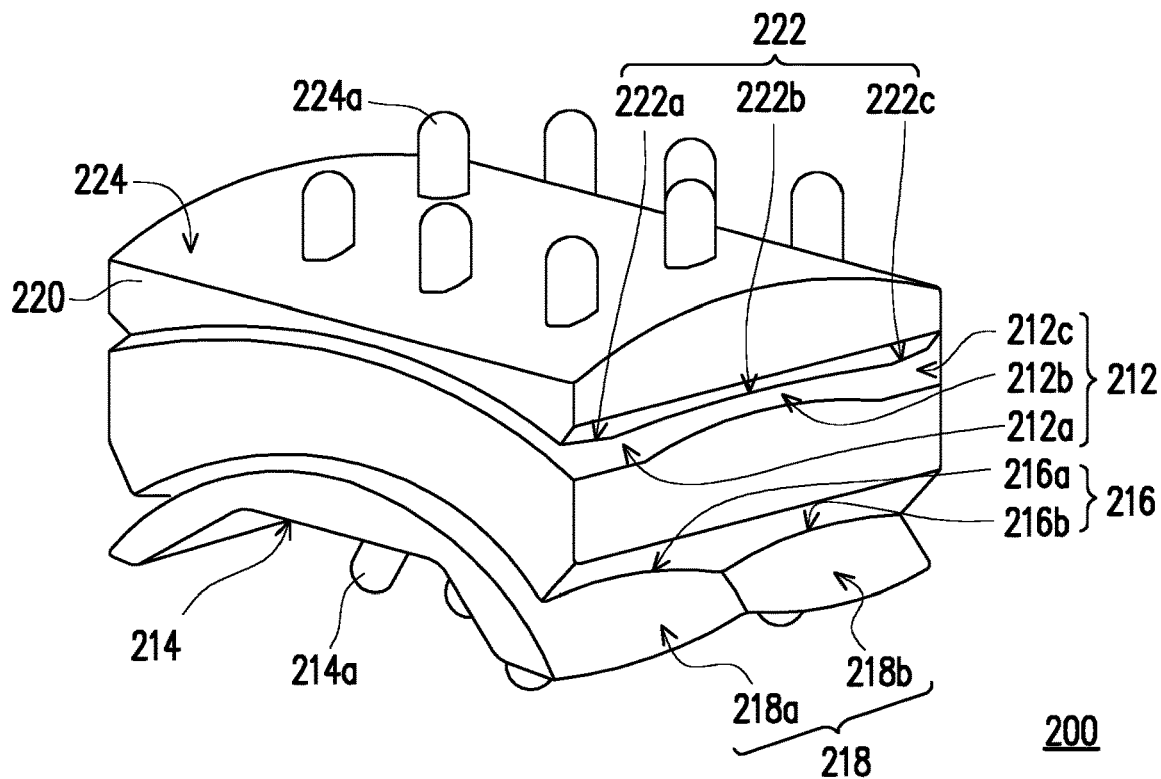
FIG. 7 is a perspective view illustrating an artificial joint of another embodiment of the disclosure.
Figure 8:
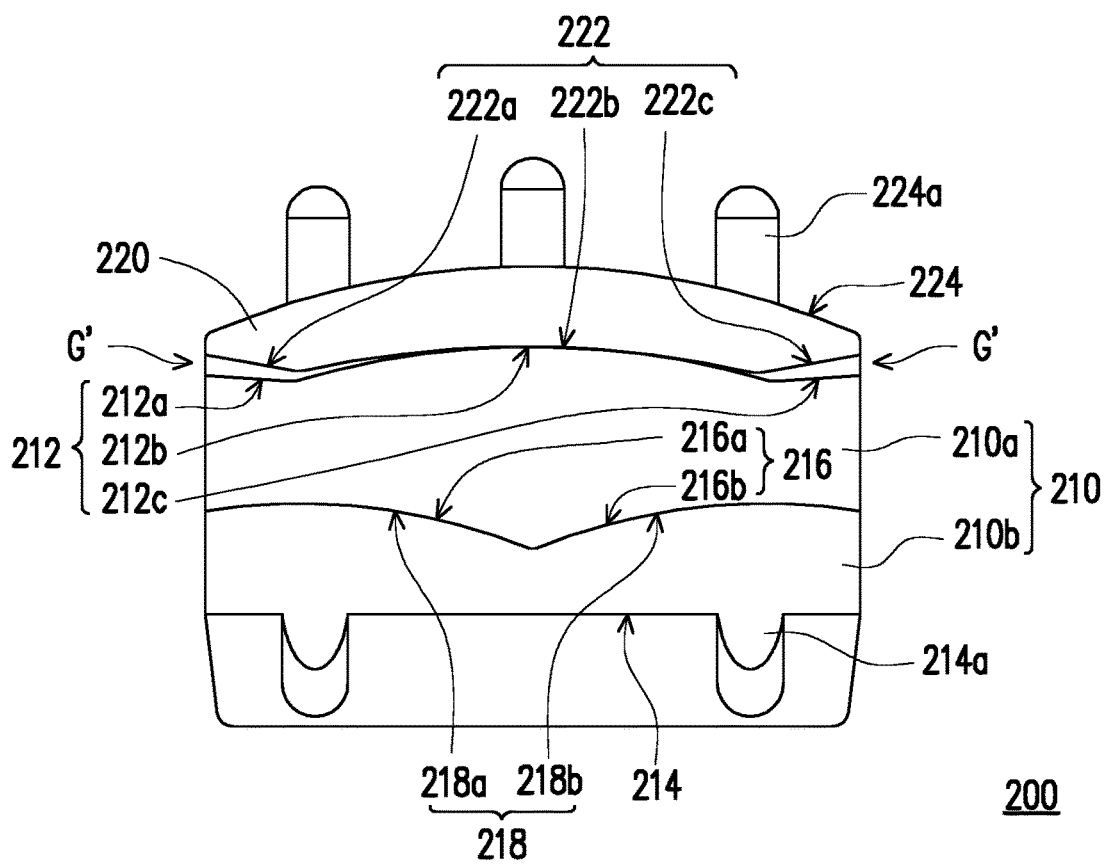
FIG. 8 is a cross-sectional view illustrating the artificial joint of FIG. 7.

FIG. 7 is a perspective view illustrating an artificial joint of another embodiment of the disclosure. FIG. 8 is a cross-sectional view illustrating the artificial joint of FIG. 7. In an artificial joint 200 of FIG. 7 and FIG. 8, the configurations and functions of a first joint assembly 210, a first contacting surface 212, a first convex arc surface 212a, a second convex arc surface 212b, a third convex arc surface 212c, a first connecting surface 214, first bone pegs 214a, a second joint assembly 220, a second contacting surface 222, a first concave arc surface 222a, a second concave arc surface 222b, a third concave arc surface 222c, a second connecting surface 224, second bone pegs 224a, and a gap G' are similar to the configurations and functions of the first joint assembly 110, the first contacting surface 112, the first convex arc surface 112a, the second convex arc surface 112b, the third convex arc surface 112c, the first connecting surface 114, the first bone pegs 114a, the second joint assembly 120, the second contacting surface 122, the first concave arc surface 122a, the second concave arc surface 122b, the third concave arc surface 122c, the second connecting surface 124, the second bone pegs 124a, and the gap G of FIG. 1 and FIG. 2 and shall not be repeatedly described here.

It is noted that, in the artificial joint 200, the first joint assembly 210 includes a contacting member 210a and a connecting member 210b. The first contacting surface 212 is formed on the contacting member 210a, and the contacting member 210a has a third contacting surface 216 opposite to the first contacting surface 212. The third contacting surface 216 includes a fourth concave arc surface 216a and a fifth concave arc surface 216b. The connecting member 210b is adapted to be connected to the first bone and has a fourth contacting surface 218. The fourth contacting surface 218 is in contact with the third contacting surface 216 and includes a fourth convex arc surface 218a and a fifth convex arc surface 218b. The fourth convex arc surface 218a and the fifth convex arc surface 218b respectively correspond to the fourth concave arc surface 216a and the fifth concave arc surface 216b. In other embodiments, the third contacting surface 216 may include three arc surfaces and the fourth contacting surface 218 may include three corresponding arc surfaces, and the disclosure is not limited thereto. Moreover, in the present embodiment, the third contacting surface 216 and the fourth contacting surface 218 can completely fit together. However, in other embodiments, a gap (similar to that between the first contacting surface 212 and the second contacting surface 222) may also be present between the third contacting surface 216 and the fourth contacting surface 218, and the disclosure is not limited thereto.

In the case where the artificial joint 200 is used as an artificial ankle joint, the connecting member 210b is a talar component used to be connected to a talus, the second joint assembly 220 is a tibial component used to be connected to a tibia, and the contacting member 210a is an insert located between the talar component and the tibial component. In the present embodiment, the material of the connecting member 210b and the second joint assembly 220 is, for example, metal, and the material of the contacting member 210a is, for example, plastic. In other embodiments, the connecting member 210b, the second joint assembly 220, and the contacting member 210a may be respectively formed of other suitable materials, and the disclosure is not limited thereto.

Figure 9:
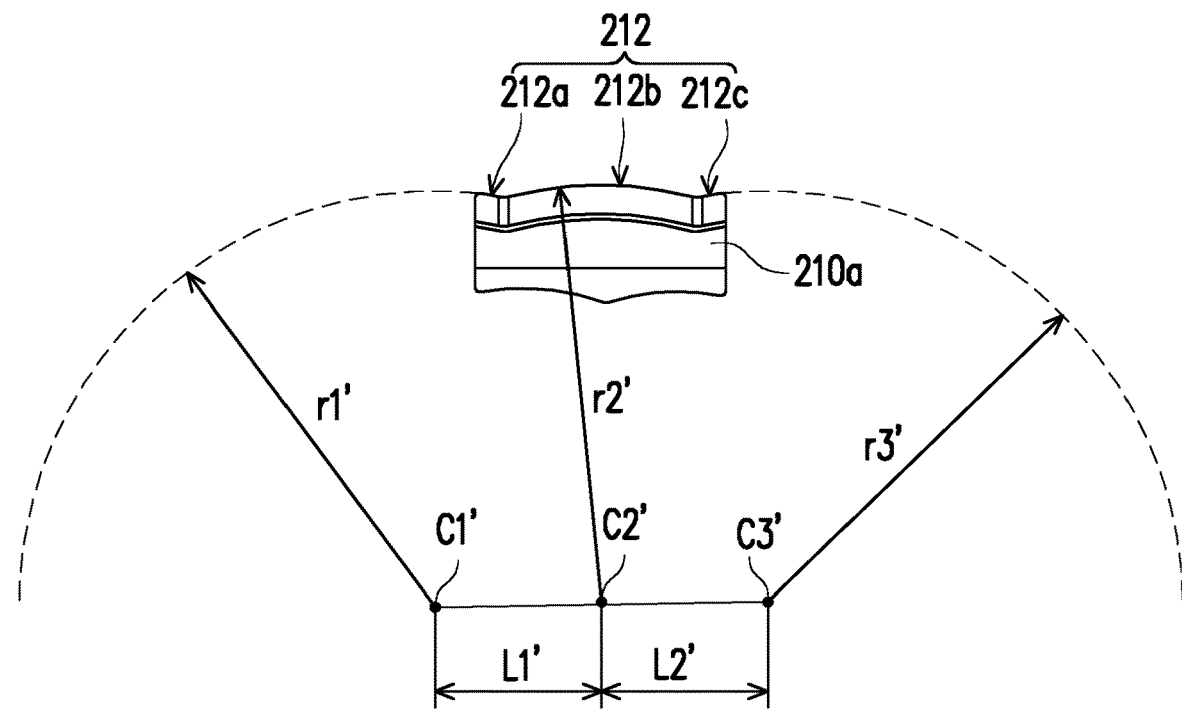
FIG. 9 is a front view illustrating a contacting member of the first joint assembly of FIG. 7.
Figure 10:
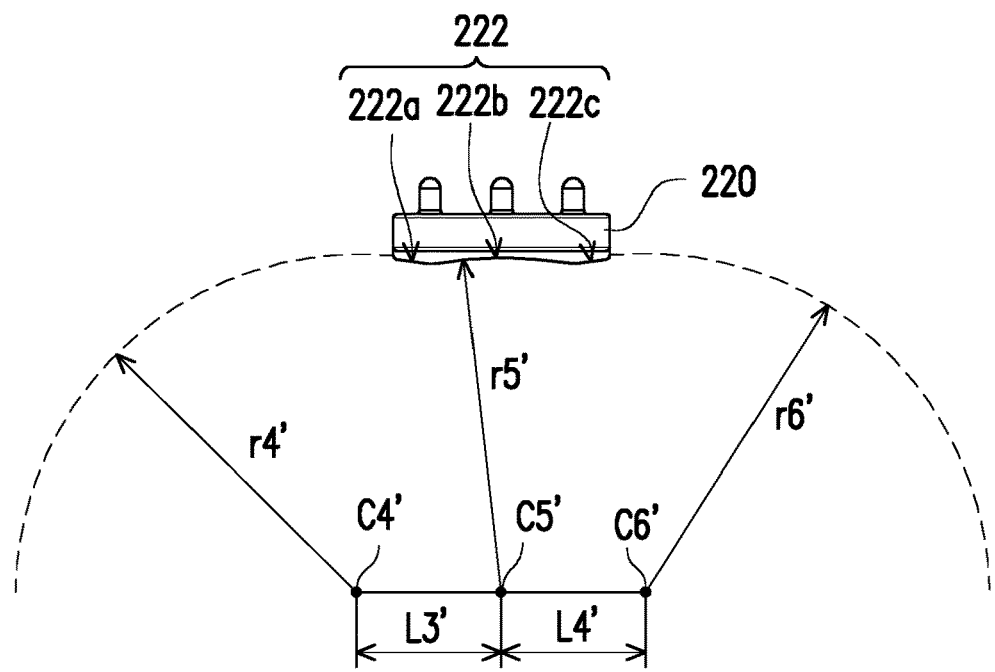
FIG. 10 is a front view illustrating a part of the structure of the second joint assembly of FIG. 7.

Designs of the arc surfaces will be detailed below. FIG. 9 is a front view illustrating the contacting member of the first joint assembly of FIG. 7. FIG. 10 is a front view illustrating a part of the structure of the second joint assembly of FIG. 7. Referring to FIG. 9 and FIG. 10, centers C1', C2', C3' of curvature of the first convex arc surface 212a, the second convex arc surface 212b, and the third convex arc surface 212c are different, and centers C4', C5', C6' of curvature of the first concave arc surface 222a, the second concave arc surface 222b, and the third concave arc surface 222c are different.

Moreover, the connecting line of the centers C1', C2' of curvature may be designed not to be parallel to the connecting line of the centers C2', C3' of curvature, and/or the connecting line of the centers C4', C5' of curvature may be designed not to be parallel to the connecting line of the centers C5', C6' of curvature. In addition, the inclination angle of the connecting line of the centers C1', C2' of curvature may be designed to be different from the inclination angle of the connecting line of the centers C4', C5' of curvature, and/or the inclination angle of the connecting line of the centers C2', C3' of curvature may be designed to be different from the inclination angle of the connecting line of the centers C5', C6' of curvature, such that the gap G' can be present respectively between the first convex arc surface 212a and the first concave arc surface 222a and between the third convex arc surface 212c and the third concave arc surface 222c as shown in FIG. 8, and allowances for inversion, eversion, internal rotation, and external rotation can thereby be provided after implantation is performed. Moreover, in other embodiments where the first convex arc surface 212a, the third convex arc surface 212c, the first concave arc surface 222a, and the third concave arc surface 222c are not spherical surfaces, the gap may similarly be present respectively between the first convex arc surface 212a and the first concave arc surface 222a and between the third convex arc surface 212c and the third concave arc surface 222c through a suitable geometric design to thereby provide allowances for inversion, eversion, internal rotation, and external rotation after implantation is performed.

More specifically, a radius r1' of curvature of the first convex arc surface 212a may be, for example, 20 to 80 mm, may be 40 to 60 mm in an embodiment, or may be designed to be 50 mm. A radius r2' of curvature of the second convex arc surface 212b may be, for example, 20 to 80 mm, may be 40 to 60 mm in an embodiment, or may be designed to be 50 mm. A radius r3' of curvature of the third convex arc surface 212c may be, for example, 20 to 80 mm, may be 40 to 60 mm in an embodiment, or may be designed to be 50 mm. A distance L1' between the center C1' of curvature of the first convex arc surface 212a and the center C2' of curvature of the second convex arc surface 212b in the horizontal direction may be, for example, 5 to 30 mm and may be 20 mm in an embodiment. A distance L2' between the center C3' of curvature of the third convex arc surface 212c and the center C2' of curvature of the second convex arc surface 212b in the horizontal direction may be, for example, 5 to 30 mm and may be 20 mm in an embodiment.

It is noted that, in the case where the connecting line of the centers C1', C2' of curvature is designed not to be parallel to the connecting line of the centers C2', C3' of curvature as described above, the inclination angle of the connecting line of the centers C1', C2' of curvature may be, for example, −4 to 4 degrees, may be −2 to 2 degrees in an embodiment, or may be designed to be 0 degrees, and the inclination angle of the connecting line of the centers C2', C3' of curvature may be, for example, −4 to 4 degrees, may be −2 to 2 degrees in an embodiment, or may be designed to be 0 degrees.

A radius r4' of curvature of the first concave arc surface 222a may be, for example, 20 to 80 mm, may be 40 to 60 mm in an embodiment, or may be designed to be 50 mm. A radius r5' of curvature of the second concave arc surface 222b may be, for example, 20 to 80 mm, may be 40 to 60 mm in an embodiment, or may be designed to be 50 mm. A radius r6' of curvature of the third concave arc surface 222c may be, for example, 20 to 80 mm, may be 40 to 60 mm in an embodiment, or may be designed to be 50 mm. A distance L3' between the center C4' of curvature of the first concave arc surface 222a and the center C5' of curvature of the second concave arc surface 222b in the horizontal direction may be, for example, 5 to 30 mm and may be 20 mm in an embodiment. A distance L4' between the center C6' of curvature of the third concave arc surface 222c and the center C5' of curvature of the second concave arc surface 222b in the horizontal direction may be, for example, 5 to 30 mm and may be 20 mm in an embodiment.

It is noted that, in the case where the connecting line of the centers C4', C5' of curvature is designed not to be parallel to the connecting line of the centers C5', C6' of curvature as described above, the inclination angle of the connecting line of the centers C4', C5' of curvature may be, for example, −2 to 6 degrees, may be 0 to 4 degrees in an embodiment, or may be designed to be 2 degrees, and the inclination angle of the connecting line of the centers C5', C6' of curvature may be, for example, −6 to 2 degrees, may be −4 to 0 degrees in an embodiment, or may be designed to be −2 degrees.

Figure 11:
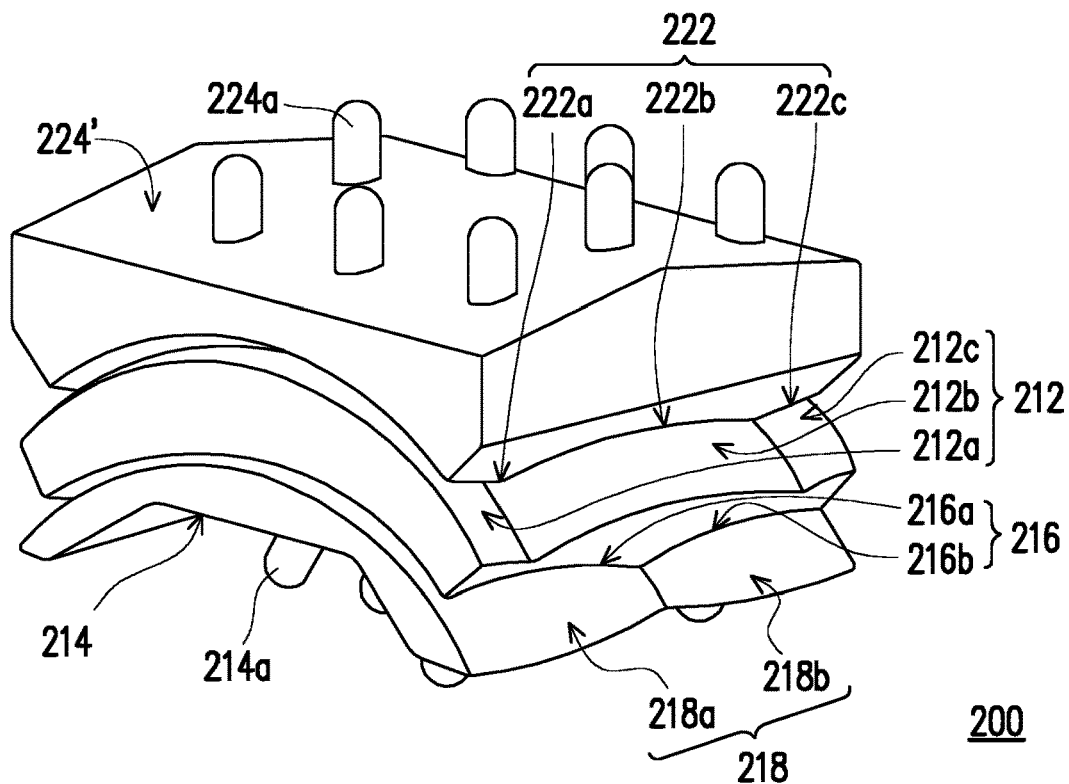
FIG. 11 is a perspective view illustrating an artificial joint of another embodiment of the disclosure.
Figure 12:
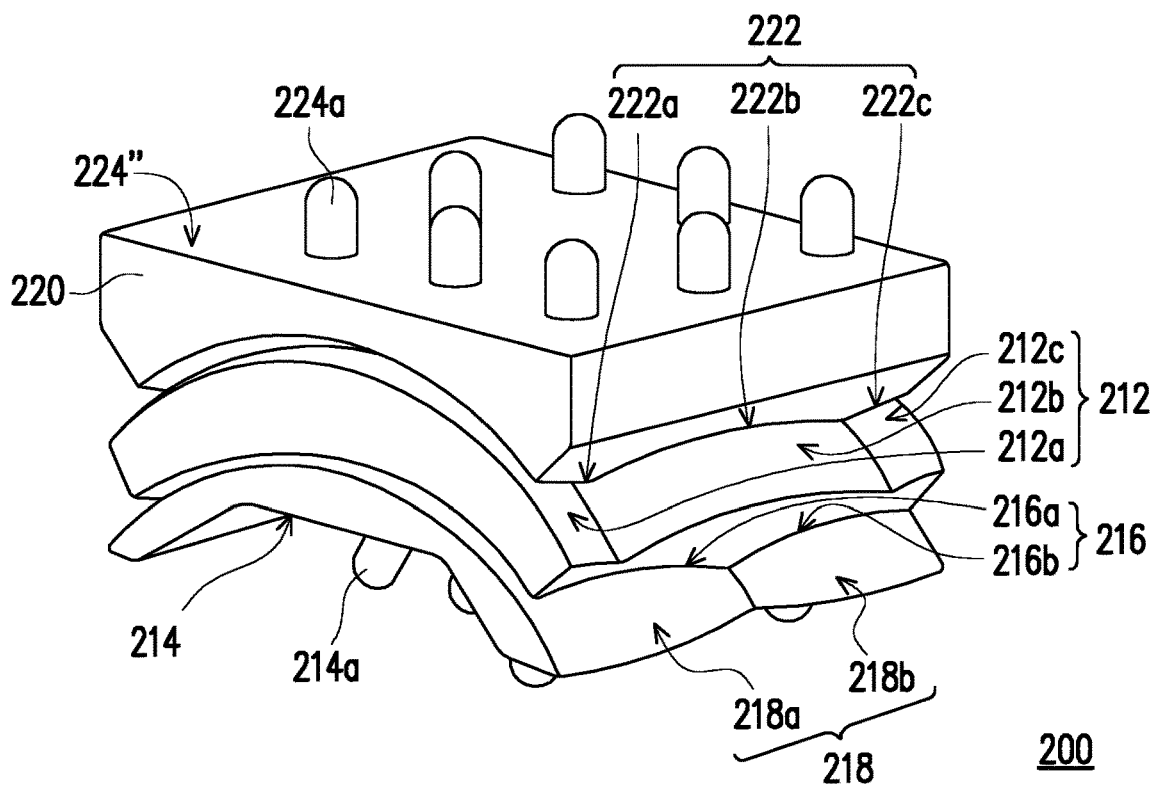
FIG. 12 is a perspective view illustrating an artificial joint of another embodiment of the disclosure.

In the present embodiment, the first connecting surface 214 of the first joint assembly 210 is a concave surface. Moreover, the second connecting surface 224 of the second joint assembly 220 is a convex arc surface to distribute the pressure between the second bone and the second joint assembly 220. However, the disclosure is not limited thereto and will be further illustrated below with reference to the drawings. FIG. 11 is a perspective view illustrating an artificial joint of another embodiment of the disclosure. The embodiment shown in FIG. 11 is similar to the embodiment shown in FIG. 7. It is noted that a second connecting surface 224' of the second joint assembly 220 of FIG. 11 is a pitched surface. FIG. 12 is a perspective view illustrating an artificial joint of another embodiment of the disclosure. The embodiment shown in FIG. 12 is similar to the embodiment shown in FIG. 7. It is noted that a second connecting surface 224" of the second joint assembly 220 of FIG. 12 is a plane.

Figure 13:
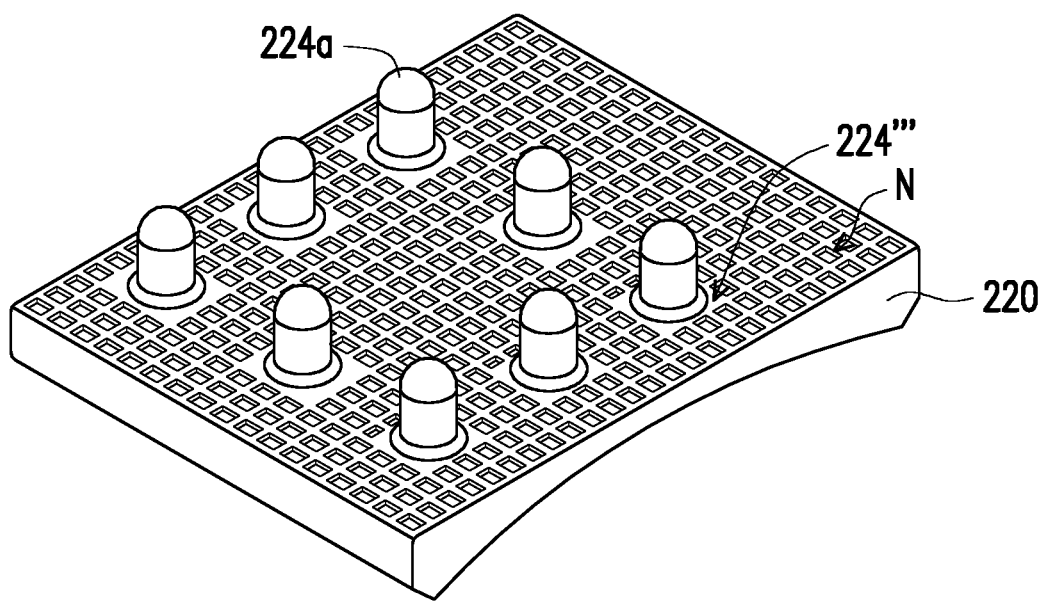
FIG. 13 is a perspective view illustrating a second joint assembly of another embodiment of the disclosure.

FIG. 13 is a perspective view illustrating a second joint assembly of another embodiment of the disclosure. It is noted that, in FIG. 13, a second connecting surface 224' of the second joint assembly 220 includes a plurality of concave holes N, such that the first bone can grow into the concave holes N to be more securely joined with the second joint assembly 220. The second connecting surface of the second joint assembly of the foregoing embodiments may all include such concave holes and the first connecting surface of the first joint assembly of the foregoing embodiments may all include such concave holes, and the disclosure is not limited thereto.

Figure 14:
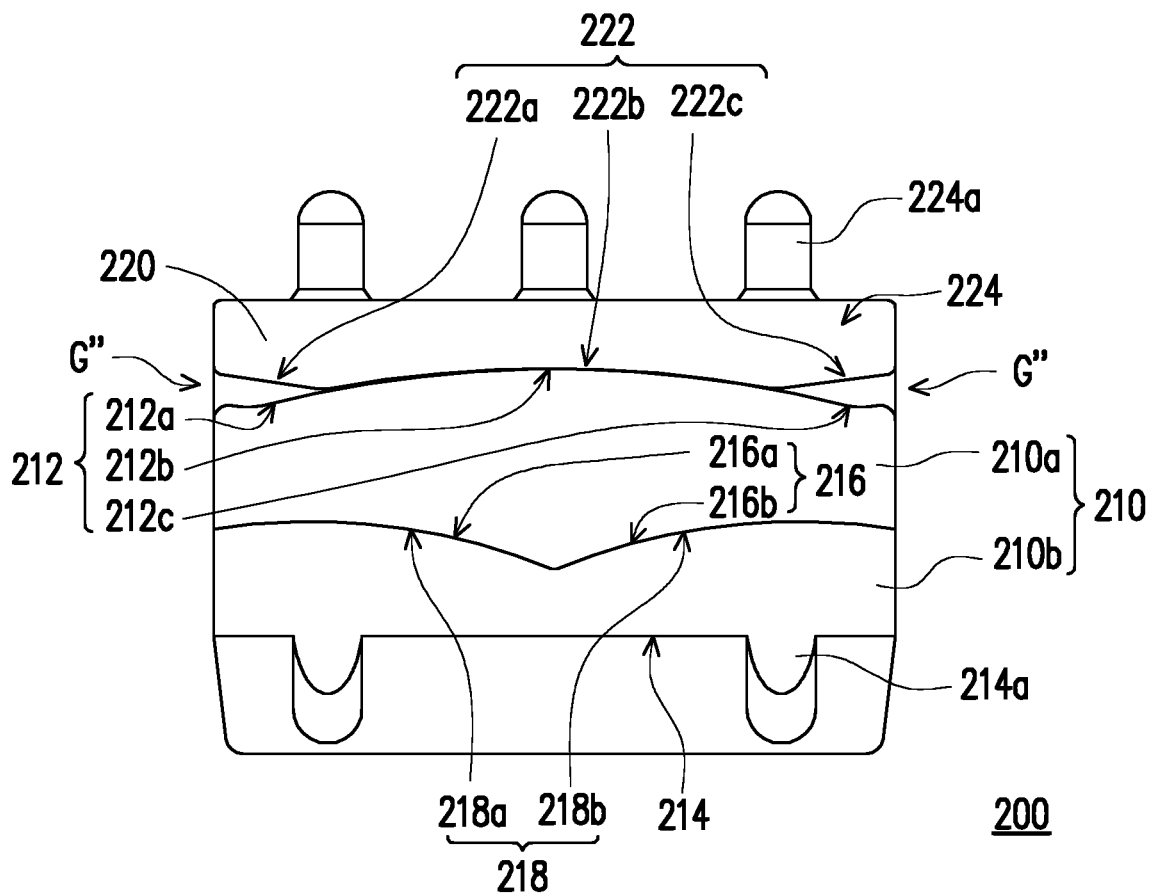
FIG. 14 is a cross-sectional view illustrating an artificial joint of another embodiment of the disclosure.
Figure 15A:
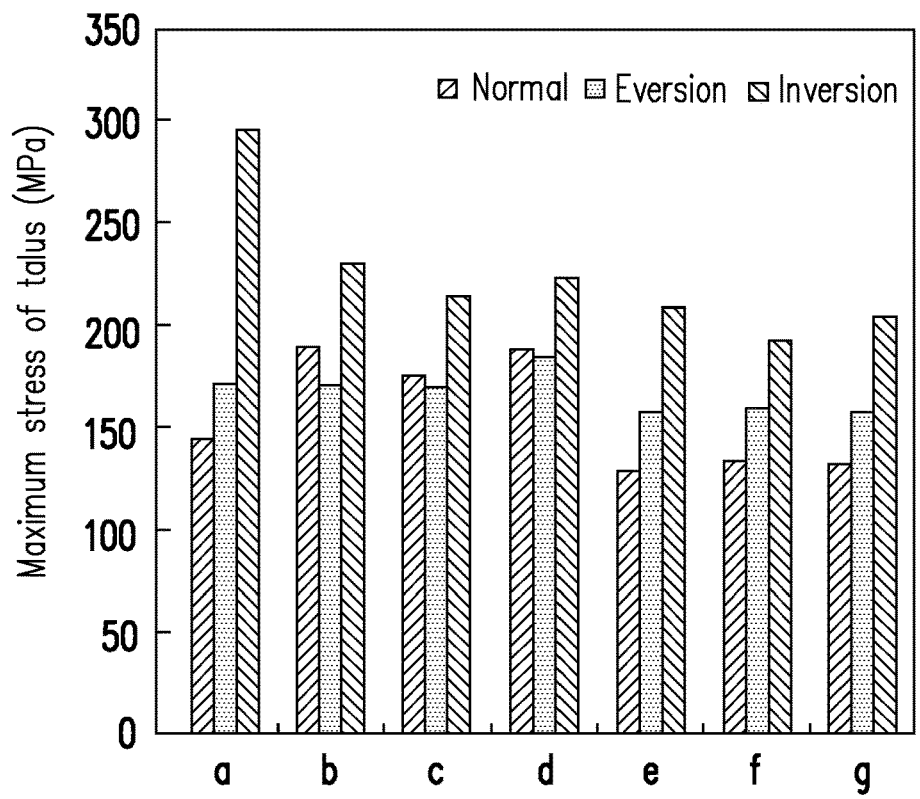
FIG. 15A to FIG. 15E are comparison graphs illustrating stress values of the artificial ankle joint of the embodiments of the disclosure and a conventional artificial ankle joint.
Figure 15B:
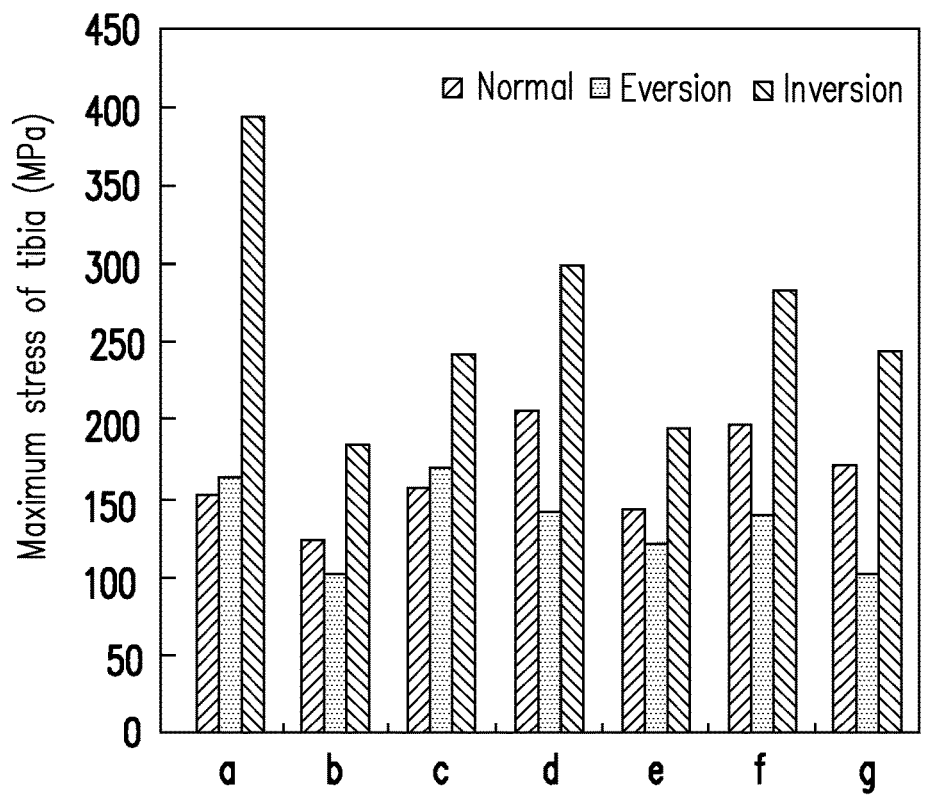
Figure 15C:
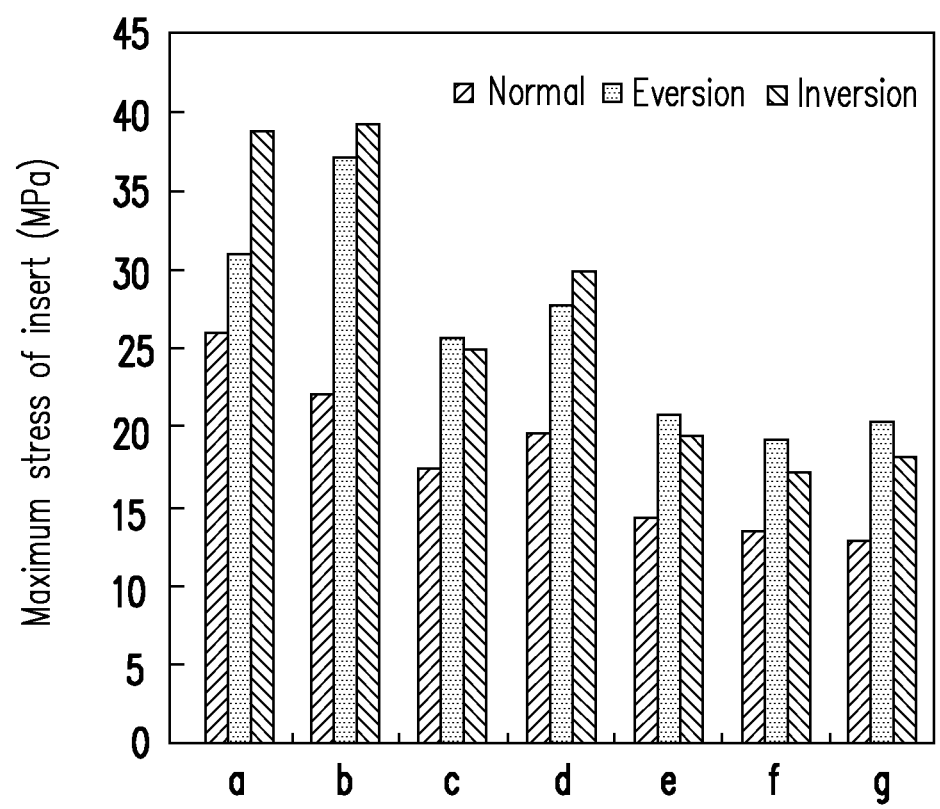
Figure 15D:
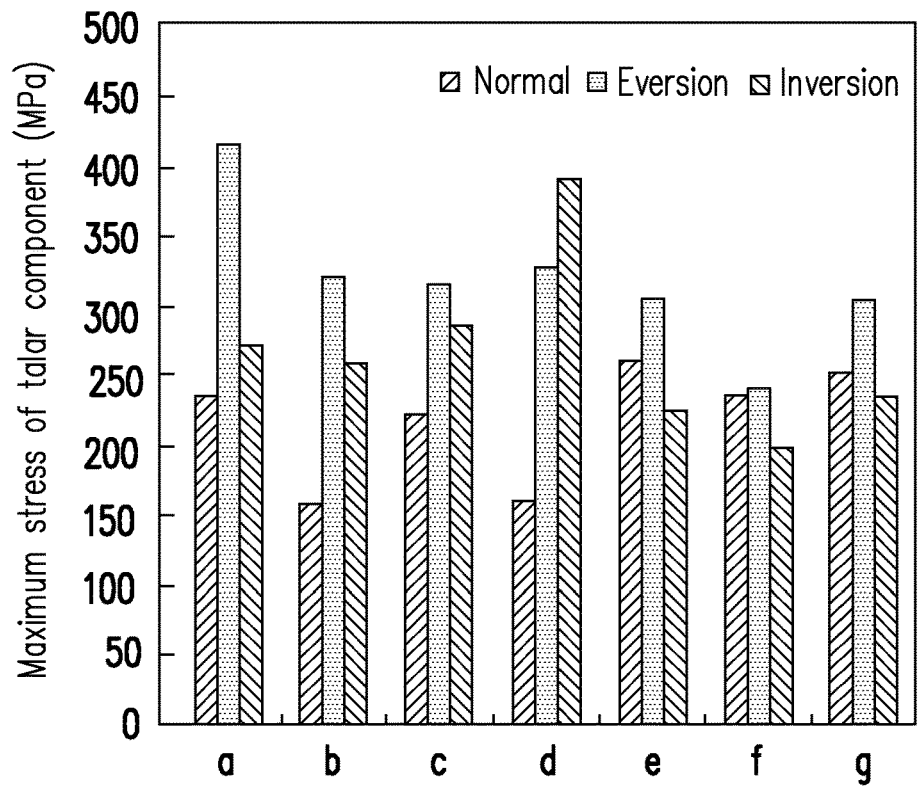
Figure 15E:
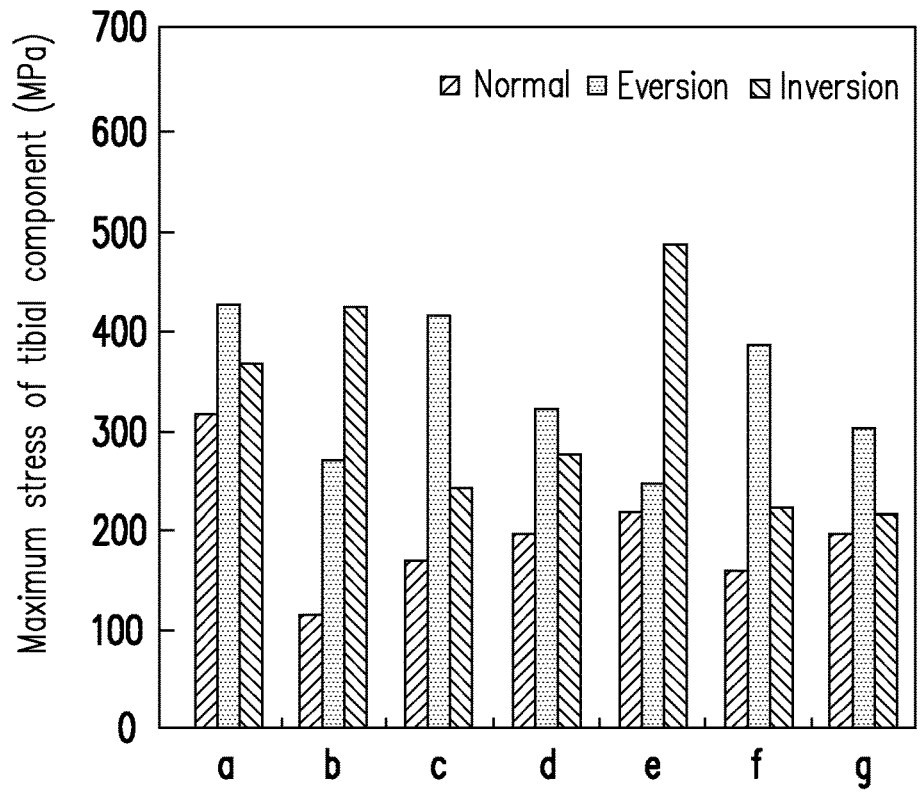

FIG. 14 is a cross-sectional view illustrating an artificial joint of another embodiment of the disclosure. It is noted that the embodiment shown in FIG. 14 has a larger gap than that in the embodiment shown in FIG. 8. Specifically, in the artificial joint 200 of FIG. 14, a larger gap G" is present between the first convex arc surface 212a of the first joint assembly 210 and the first concave arc surface 222a of the second joint assembly 220 and between the third convex arc surface 212c of the first joint assembly 210 and the third concave arc surface 222c of the second joint assembly 220, such that the artificial joint 200 can have greater inversion angle allowance and eversion angle allowance. For example, the inversion angle allowance and the eversion angle allowance of the artificial joint 200 of the embodiment shown in FIG. 8 are both, for example, 2 degrees, while the inversion angle allowance and the eversion angle allowance of the artificial joint 200 of the embodiment shown in FIG. 14 are both, for example, 4 degrees. The change in the allowance is achieved by designing the inclination angle of the connecting line of the centers C1', C2' of curvature to be different from the inclination angle of the connecting line of the centers C4', C5' of curvature, and designing the inclination angle of the connecting line of the centers C2', C3' of curvature to be different from the inclination angle of the connecting line of the centers C5', C6' of curvature as described above. In other embodiments, the inversion angle allowance and the eversion angle allowance may be designed to be greater, smaller, or non-existent, which may be tested and selected by the surgeon in a joint replacement surgery and is not limited in the disclosure.

Stress values of the artificial ankle joint of the foregoing embodiments and the conventional artificial ankle joint will be compared with reference to the drawings, wherein a smaller stress value means that wearing and loosening are less likely to occur. FIG. 15A to FIG. 15E are comparison graphs illustrating stress values of the artificial ankle joint of the embodiments of the disclosure and a conventional artificial ankle joint. FIG. 15A to FIG. 15E respectively show the maximum stress values of the talus, the tibia, the insert, the talar component, and the tibial component and all indicate the stress values of the artificial joint in an eversion state, an inversion state, and a normal (non-inversion and non-eversion) state. Specifically, "a" corresponds to the conventional artificial ankle joint. The conventional artificial ankle joint does not have the design of three arc surfaces of the foregoing embodiments, but has the common design of two arc surfaces. "b to g" respectively correspond to the embodiments shown in FIG. 5, FIG. 6, FIG. 1, FIG. 11, FIG. 12, and FIG. 7. According to FIG. 15A to FIG. 15E, the stress values of the artificial ankle joint having the design of three arc surfaces of the embodiments of the disclosure are superior to the stress values of the conventional artificial ankle joint having the design of two arc surfaces in overall performance.

Figure 16:
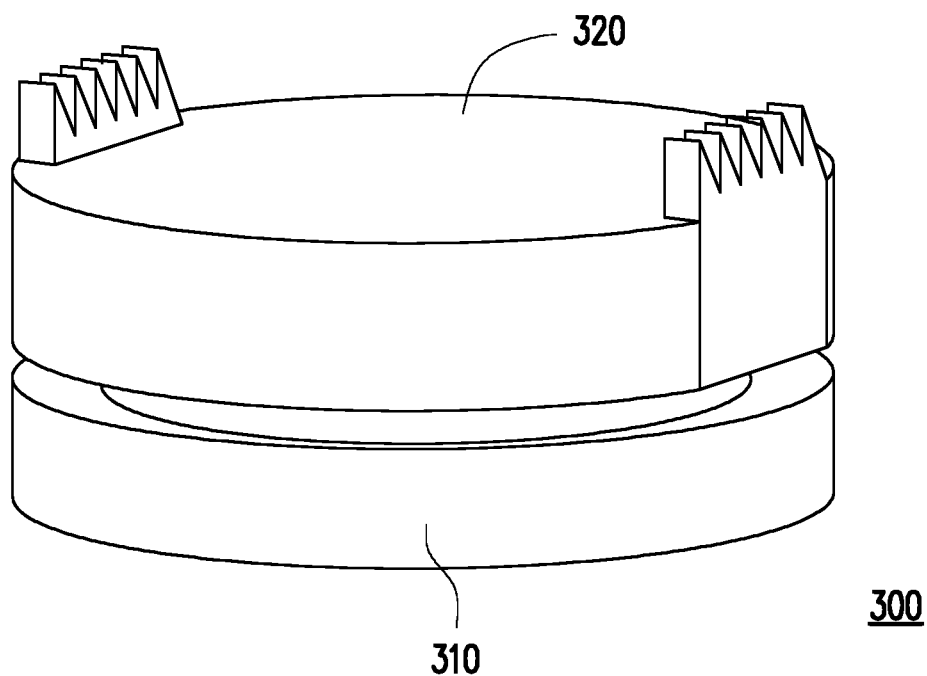
FIG. 16 is a perspective view illustrating an artificial joint of another embodiment of the disclosure.
Figure 17:
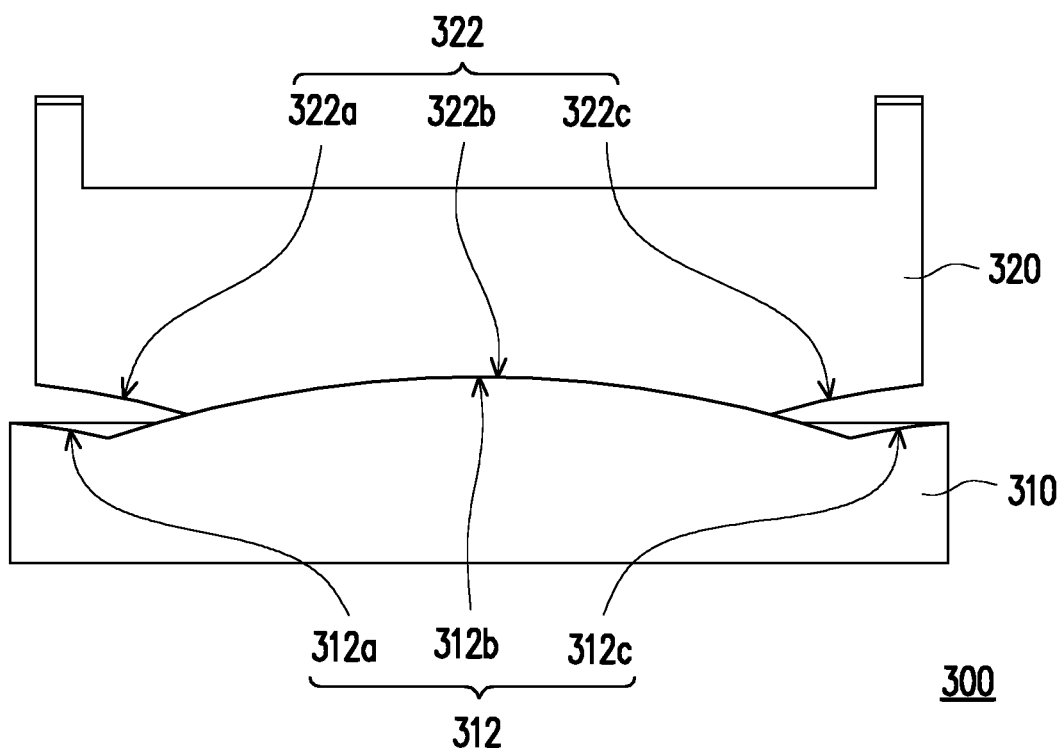
FIG. 17 is a cross-sectional view illustrating the artificial joint of FIG. 16.

FIG. 16 is a perspective view illustrating an artificial joint of another embodiment of the disclosure. FIG. 17 is a cross-sectional view illustrating the artificial joint of FIG. 16. In an artificial joint 300 shown in FIG. 16 and FIG. 17, the configurations and functions of a first joint assembly 310, a first contacting surface 312, a first convex arc surface 312a, a second convex arc surface 312b, a third convex arc surface 312c, a second joint assembly 320, a second contacting surface 322, a first concave arc surface 322a, a second concave arc surface 322b, and a third concave arc surface 322c are similar to the configurations and functions of the first joint assembly 110, the first contacting surface 112, the first convex arc surface 112a, the second convex arc surface 112b, the third convex arc surface 112c, the second joint assembly 120, the second contacting surface 122, the first concave arc surface 122a, the second concave arc surface 122b, and the third concave arc surface 122c of FIG. 1 and shall not be repeatedly described here. Specifically, the second convex arc surface 312b and the second concave arc surface 322b are, for example, spherical surfaces, the first convex arc surface 312a and the third convex arc surface 312c collectively form a torus, and the first concave arc surface 322a and the third concave arc surface 322c collectively form a torus. It is noted that the artificial joint 300 is not used as an artificial ankle joint. The artificial joint 300 is adapted to serve as an artificial vertebral column joint used to be connected to two vertebrae.

Figure 18:
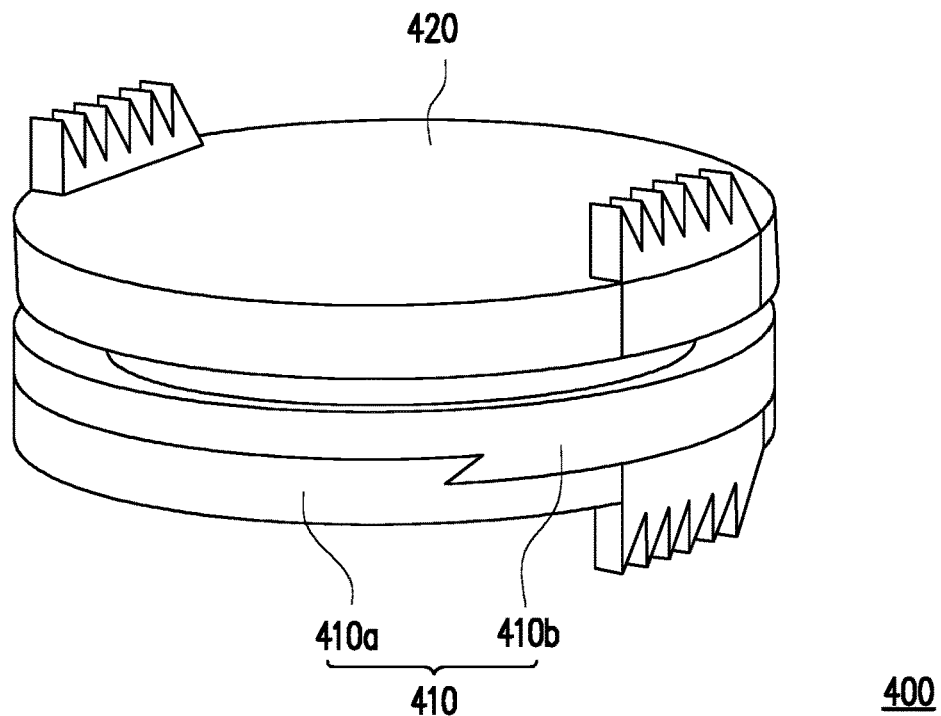
FIG. 18 is a perspective view illustrating an artificial joint of another embodiment of the disclosure.
Figure 19:
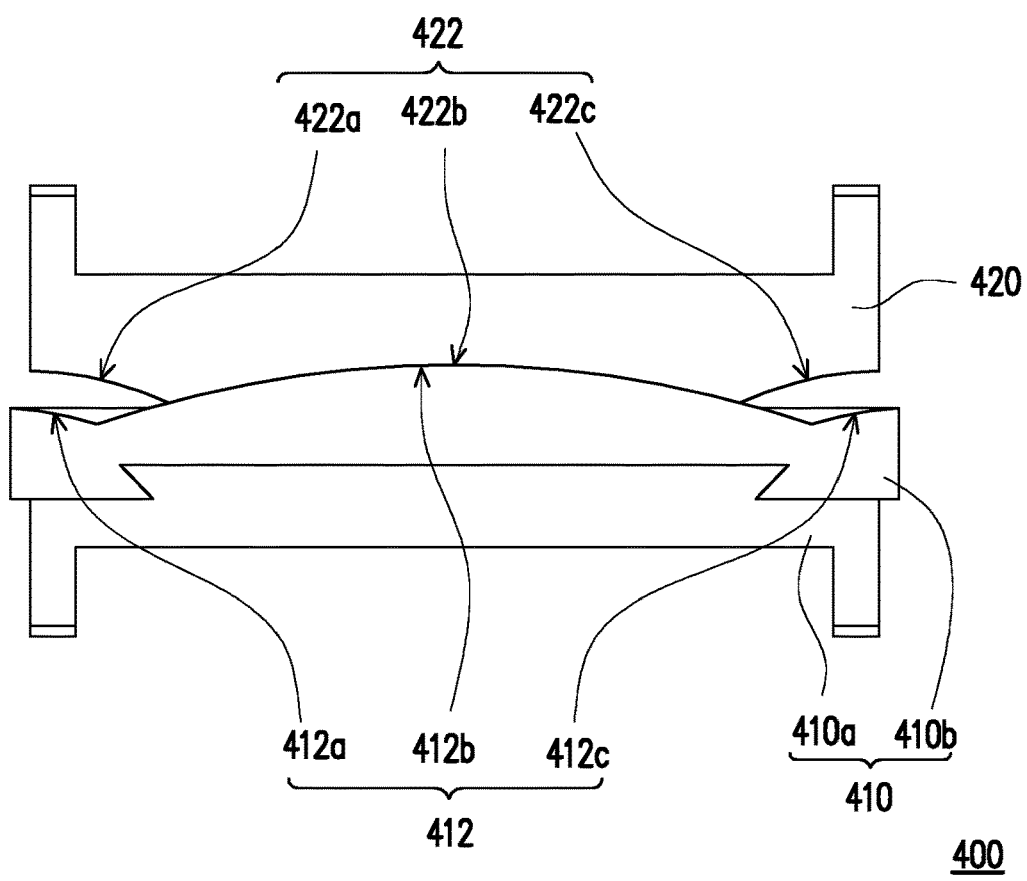
FIG. 19 is a cross-sectional view illustrating the artificial joint of FIG. 18.

FIG. 18 is a perspective view illustrating an artificial joint of another embodiment of the disclosure. FIG. 19 is a cross-sectional view illustrating the artificial joint of FIG. 18. In an artificial joint 400 of FIG. 18 and FIG. 19, the configurations and functions of a first joint assembly 410, a first contacting surface 412, a first convex arc surface 412a, a second convex arc surface 412b, a third convex arc surface 412c, a second joint assembly 420, a second contacting surface 422, a first concave arc surface 422a, a second concave arc surface 422b, and a third concave arc surface 422c are similar to the configurations and functions of the first joint assembly 310, the first contacting surface 312, the first convex arc surface 312a, the second convex arc surface 312b, the third convex arc surface 312c, the second joint assembly 320, the second contacting surface 322, the first concave arc surface 322a, the second concave arc surface 322b, and the third concave arc surface 322c of FIG. 16 and FIG. 17 and shall not be repeatedly described here. It is noted that, in the artificial joint 400, the first joint assembly 410 includes a connecting member 410a and a contacting member 410b. The first contacting surface 412 is formed on the contacting member 410b. The connecting member 410a and the contacting member 410b are fixed together and are adapted to be connected to the vertebral column joint. In other embodiments, the connecting member 410a and the contacting member 410b may be configured to be slidable with respect to each other, and the disclosure is not limited thereto.

According to the foregoing embodiments, the contacting surfaces of the artificial joint of the disclosure have the design of three arc surfaces. The gap between the contacting surfaces may be formed through variations in the design of relative positions between the arc surfaces to provide allowance for motion of the artificial joint. Therefore, in addition to the application examples of the ankle joint and the vertebral column joint listed above, the disclosure is also applicable to the knee joint, the hip joint, etc. and is not limited thereto.

Furthermore, in the disclosure, the three convex arc surfaces of the first joint assembly respectively correspond to the three concave arc surfaces of the second joint assembly. The convex arc surface and the concave arc surface located in the middle may be in contact with each other to provide support and can undergo flexion/extension motions on the sagittal plane. A gap may be present between the convex arc surfaces and the concave arc surfaces located on the outer sides to further increase the space for relative motion of the first joint assembly and the second joint assembly. The space for relative motion may include that of internal rotation, external rotation, eversion motion, and inversion motion. Accordingly, additional stress between the first joint assembly and the second joint assembly due to structural restriction of bones and ligaments can be reduced, and wearing and loosening of the artificial joint can be mitigated. In addition, the convex arc surface and the concave arc surface located in the middle may be designed to have a greater area to provide the main weight-bearing function. The convex arc surfaces and the concave arc surfaces located on the outer sides having a smaller area can provide inversion and eversion stability.

Although the embodiments are already disclosed as above, these embodiments should not be construed as limitations on the scope of the disclosure. It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An artificial joint comprising:
   a first joint assembly adapted to be connected to a first bone and having a first contacting surface, wherein the first contacting surface comprises a first convex arc surface, a second convex arc surface, and a third convex arc surface; and
   a second joint assembly adapted to be connected to a second bone and having a second contacting surface, wherein the second contacting surface is in contact with the first contacting surface and comprises a first concave arc surface, a second concave arc surface, and a third concave arc surface, and the first concave arc surface, the second concave arc surface, and the third concave arc surface respectively correspond to the first convex arc surface, the second convex arc surface, and the third convex arc surface,
   wherein the first joint assembly is adapted to be connected to the first bone in a first direction, and a connecting line of a center of curvature of the first convex arc surface, a center of curvature of the second convex arc surface, and a center of curvature of the third convex arc surface is not perpendicular to the first direction, or wherein the second joint assembly is adapted to be connected to the second bone in a second direction, and a connecting line of a center of curvature of the first concave arc surface, a center of curvature of the second concave arc surface, and a center of curvature of the third concave arc surface is not perpendicular to the second direction.

2. The artificial joint according to claim 1, wherein centers of curvature of the first convex arc surface, the second convex arc surface, and the third convex arc surface are different, and centers of curvature of the first concave arc surface, the second concave arc surface, and the third concave arc surface are different.

3. The artificial joint according to claim 1, wherein the first convex arc surface, the second convex arc surface, and the third convex arc surface are all convex spherical surfaces, and the first concave arc surface, the second concave arc surface, and the third concave arc surface are all concave spherical surfaces.

4. The artificial joint according to claim 1, wherein the second convex arc surface is connected between the first convex arc surface and the third convex arc surface, and the second concave arc surface is connected between the first concave arc surface and the third concave arc surface.

5. The artificial joint according to claim 4, wherein an area of the second convex arc surface is greater than an area of the first convex arc surface and greater than an area of the third convex arc surface, and an area of the second concave arc surface is greater than an area of the first concave arc surface and greater than an area of the third concave arc surface.

6. The artificial joint according to claim 4, wherein when the second convex arc surface and the second concave arc surface are in normal contact with each other, a gap is present between the first convex arc surface and the first concave arc surface, and another gap is present between the third convex arc surface and the third concave arc surface.

7. The artificial joint according to claim 1, wherein the first joint assembly has a first connecting surface opposite to the first contacting surface, and the first connecting surface comprises a plurality of bone pegs and is adapted to be connected to the first bone through the bone pegs.

8. The artificial joint according to claim 1, wherein the second joint assembly has a second connecting surface opposite to the second contacting surface, and the second connecting surface comprises a plurality of bone pegs and is adapted to be connected to the second bone through the bone pegs.

9. The artificial joint according to claim 1, wherein the first joint assembly has a first connecting surface opposite to the first contacting surface, and the first connecting surface is a concave surface and is adapted to be connected to the first bone.

10. The artificial joint according to claim 1, wherein the second joint assembly has a second connecting surface opposite to the second contacting surface, and the second connecting surface is a convex surface and is adapted to be connected to the second bone.

11. The artificial joint according to claim 1, wherein the second joint assembly has a second connecting surface opposite to the second contacting surface, and the second connecting surface is a plane and is adapted to be connected to the second bone.

12. The artificial joint according to claim 1, wherein the first joint assembly has a first connecting surface opposite to the first contacting surface, the second joint assembly has a second connecting surface opposite to the second contacting surface, the first connecting surface is adapted to be connected to the first bone, the second connecting surface is adapted to be connected to the second bone, and at least one of the first connecting surface and the second connecting surface comprises a plurality of concave holes.

13. The artificial joint according to claim 1, wherein the first joint assembly comprises a contacting member and a connecting member, the first contacting surface is formed on the contacting member, the contacting member has a third contacting surface opposite to the first contacting surface, the third contacting surface comprises a fourth concave arc surface and a fifth concave arc surface, the connecting member is adapted to be connected to the first bone and has a fourth contacting surface, the fourth contacting surface is in contact with the third contacting surface and comprises a fourth convex arc surface and a fifth convex arc surface, and the fourth concave arc surface and the fifth concave arc surface respectively correspond to the fourth convex arc surface and the fifth convex arc surface.

14. The artificial joint according to claim 1, wherein the first bone is a talus, and the second bone is a tibia.

15. The artificial joint according to claim 1, wherein the first bone and the second bone are vertebrae.

* * * * *